United States Patent
Cipolletti

(10) Patent No.: US 8,808,458 B2
(45) Date of Patent: Aug. 19, 2014

(54) CONTINUOUS PROCESS FOR THE PREPARATION OF CRYSTALLINE LACTULOSE

(75) Inventor: Giovanni Cipolletti, Milan (IT)

(73) Assignee: Fresenius Kabi Austria GmbH, Graz-Puntigam (AU)

( * ) Notice: Subject to any disclaimer, the term of this patent is extended or adjusted under 35 U.S.C. 154(b) by 891 days.

(21) Appl. No.: 12/291,769

(22) Filed: Nov. 12, 2008

(65) Prior Publication Data

US 2009/0120430 A1   May 14, 2009

(30) Foreign Application Priority Data

Nov. 14, 2007  (EP) .................................... 07425720

(51) Int. Cl.
*C13B 30/06* (2011.01)
(52) U.S. Cl.
USPC ............................................................ 127/56
(58) Field of Classification Search
None
See application file for complete search history.

(56) References Cited

U.S. PATENT DOCUMENTS 4,536,221 A    8/1985  Carobbi et al.
5,480,491 A *  1/1996  Bimbi ............................ 127/61

FOREIGN PATENT DOCUMENTS

| EP | 0 318 630 A1 | 1/1988 |
| EP | 0 480 519 A1 | 10/1991 |
| EP | 0 532 173 A3 | 8/1992 |
| EP | 0 685 486 A1 | 6/1993 |
| EP | 0 622 374 A1 | 4/1994 |
| WO | WO 94/29476 A | 12/1994 |

OTHER PUBLICATIONS

Spivak et al., "Preparation of N-Acetyl-D-mannosamine and . . . " from the Rackham Arthritis Research Unit and Dept. of Biological Chemistry, University of Michigan, May 20, 1959.

Lee et al., "Production of N-Acetylneuraminic Acid from N-Acetylgulcosamine . . . " Enzyme and Microbial Technologty 35 (2004) 121-125.

Mack et al., "2-Acetamido-2-deoxy-D-gluco- and -D-mannofuranose: . . . " Carbohydrate Research, 175 (1988) 311-316.

* cited by examiner

*Primary Examiner* — Melvin C Mayes
*Assistant Examiner* — Stefanie Cohen
(74) *Attorney, Agent, or Firm* — Abelman, Frayne & Schwab

(57) ABSTRACT

The present invention concerns a process that can be realised continuously for the preparation of anhydrous crystalline lactulose from commercial aqueous syrups that contain it, characterised in that the crystallisation and consequent separation of the high-purity lactulose with high yields from the syrup is triggered by mixing the ore pulp (or recycled ore pulp), obtained from a previous lactulose crystallisation phase, with the syrup itself.

12 Claims, No Drawings

CONTINUOUS PROCESS FOR THE PREPARATION OF CRYSTALLINE LACTULOSE

FIELD OF THE INVENTION

This invention concerns an industrial process that can be carried out continuously with high yields, for the preparation of high-purity crystalline lactulose, by crystallisation from aqueous syrups available on the market.

PRIOR ART

Lactulose, or 4-O-P-D-galactopyranosyl-D-fructofuranose, is a semi-synthetic disaccharide used in the form of syrup or as a crystalline product for its laxative effects, for its efficacy in hepatic dysfunctions and in particular in portosystemic encephalopathy, or as a sweetening substance.

The lactulose syrups currently available on the market are not pure, but contain more or less high quantities of other carbohydrates, in particular galactose and lactose: up to 8% by weight of galactose, up to 5% by weight of lactose, and up to 10% by weight of other carbohydrates.

So generally the percentage quantity of carbohydrates other than lactulose contained in commercial syrups is relatively high.

The use of products containing other carbohydrates, besides lactulose, for therapies that require the administration of lactulose alone may be problematic and not acceptable, for example in patients suffering from diabetes or who require a diet without galactose and/or without lactose.

The need was therefore felt to have a high-purity lactulose, in particular for use in the pharmaceutical field. For this purpose various processes have been proposed for extracting lactulose from syrups.

As described in U.S. Pat. No. 4,536,221, various known processes for purifying lactulose are based on crystallisation from alcoholic solvents, in particular from ethanol.

However, the lactulose crystals obtained from alcohols always contain a certain amount of solvent that cannot be eliminated, probably due to the formation of hydrogen bonds between the OH groups of the sugar and the OH groups of the solvent.

Processes are also known for recovering lactulose directly from aqueous solutions, based on their concentration by vacuum drying, freeze drying and spray drying. Among these we mention:

the process described in the Japanese patent application JP no. 61.104.800 which comprises the concentration of an aqueous solution containing at least 60% lactulose, the addition to the obtained concentrate of crystalline germs at 60°-110° C. and, after mixing and pulverisation, obtaining a powder containing lactulose crystals;

the process described in the European patent application EP-A-333,295 for preparing solid lactulose from an aqueous syrup by reducing the water content to a maximum of 10% by hot evaporation, followed by cooling, grinding, sieving or crumbling of the solid product obtained;

the process described in the European patent application EP-A-480,519 which describes a method for solidifying lactulose from aqueous solutions, by evaporating the water they contain, with conversion of the treated material into a flowing powder. The solidification of lactulose may be triggered by adding crystalline germs, preferably in a quantity of 15% by weight on the dry residue;

the process described in the Japanese patent application JP no. 2,200,693, which contemplates the crystallisation of lactulose from a condensed syrup, followed by drying of the condensate at reduced pressure and pulverisation of the dry product obtained.

Substantially, the above-mentioned processes are based on techniques of evaporation and concentration of the starting syrup and they are profoundly different from crystallisation, as they simply involve the solidification of the solutes without resulting, as in the case of crystallisation, in the elimination of the undesired secondary components contained in the mother liquors.

Consequently the processes based on concentration can simply supply lactulose with the same degree of purity as the starting material, not being suitable for the preparation of high-purity lactulose from commercial syrups which, as stated above, contain high quantities of other carbohydrates. The above processes do not allow pure crystalline lactulose to be obtained without resorting to a process of crystallisation from alcohol.

A process that involves real crystallisation from water, without resorting to the use of alcoholic solvents, is described in the European patent application EP-318,630 of the Applicant, and it is a process which really allows crystalline lactulose to be obtained with a high degree of purity (≥98%) and in a non hygroscopic form. However, this process cannot be applied if the aqueous syrup from which the lactulose is to be crystallised has a content of carbohydrates, other than lactulose, higher than 14% by weight of the lactulose itself.

In the case of lactulose syrups having a quantity of carbohydrates higher than that limit value it is necessary to reduce the content of carbohydrates other than lactulose in the starting syrup to values lower than the one indicated above, carrying out a purification treatment of the aqueous syrup with one of the many known methods. This considerably affects the industrial process and the costs.

A later patent by the same Applicant, EP 622,374, has made it possible to overcome this limit and to use, for extracting lactulose, commercial syrups with a content of other sugars even higher than 14%, using syrups with 70°-80° Brix and triggering crystallisation with 5-30% of crystalline lactulose trihydrate prepared separately, in a pure form. Up till today this is the best known process for obtaining high-purity lactulose from syrup.

DETAILED DESCRIPTION OF THE INVENTION

The Applicant has now found, and it is the object of this invention, a new process for the crystallisation of high-purity lactulose from commercial syrups that contain it, which may be industrially carried out on a continuous basis, with notable simplification of the operative phases and with appreciably higher yields than with EP 622,373 which, as stated above, is the best process currently known, industrially realised.

The new process contemplates the crystallisation of lactulose from commercial aqueous syrups, which therefore contain, besides lactulose, notable quantities of other carbohydrates. Syrups containing carbohydrates other than lactulose, in quantities between 10 and 30% with respect to lactulose, are generally treated. The carbohydrates prevalently present are: lactose (LTS), galactose (GLT), tagatose (TGT), epilactose (EPL), fructose (FRT), with a decidedly higher percentage for lactose and galactose.

The syrups to be treated must be concentrated to a saccharimetric degree between 70° and 80° Brix and then a lactulose suspension is added, obtained from the processing cycle as ore pulp of the precipitated and separated crystalline lactulose, at a temperature between 15° and 25° C., stirring.

Stirring the ore pulp triggers the crystallisation of the lactulose contained in the aqueous syrup, thus producing a new patch of crystalline lactulose with purity higher than 98%, generally 99% or higher, and a new suspension which, suitably dosed, returns into the cycle. In this way an extremely simple continuous cycle is obtained, with which crystalline lactulose is created with a content of other carbohydrates lower than 1%, and the crystallisation suspension (suitably regulated) is used to trigger the crystallisation of a new batch of lactulose aqueous syrup, without adding crystalline triggering agents from outside the cycle.

It is quite surprising that by adding to the lactulose aqueous syrup a triggering agent composed not of pure crystalline lactulose but of an ore pulp of lactulose left over from the processing cycle and therefore containing the other carbohydrates contained in the starting aqueous syrup, a preferential and selective crystallisation of lactulose is induced, with respect to the other carbohydrates present in the syrup, obtaining a high-purity crystalline lactulose with higher yields than those obtained up until today by triggering with notable quantities of pure crystalline lactulose trihydrate.

It is in fact known that in crystallisation processes, once the right solvent and the right crystallisation conditions have been identified with relation to:
concentration of the desired product in the matrix used
crystallisation temperature
it is necessary to trigger the crystallisation of the desired product with a quantity, even a small one, of crystals of the same product.

In particular, when working in the field of sugars, the crystallisation conditions are achieved in considerably long periods of time, so the "random self-triggering" of the solutes having a lower $K_{ps}$ than the product to be crystallised is highly probable, with the result that the crystalline mass recovered is still polluted by these solutes, that is by the undesired carbohydrates.

The new process according to the present invention is described in detail below.

A commercial aqueous syrup of lactulose is concentrated to bring its saccharimetric degree to a value between 70° and 80° Brix and then, at a temperature between 15° and 25° C., a quantity of lactulose suspension is added (ore pulp obtained from the previous phase of crystallisation of the lactulose) between 5 and 10% by weight with respect to the lactulose contained in the syrup treated. The mass is cooled and is kept stirring for a variable time, roughly about 150 to 400 hours, depending on the composition of the starting syrup. A suspension is obtained which is centrifuged, giving origin to a solid product which is dried and which when analysed proves to be crystalline lactulose with a content of other carbohydrates of less than 1% by weight and a minimum content of lactulose on the anhydrous product of 98.5%.

More particularly the following phases are realised:
a) the commercial aqueous syrup of lactulose is subjected, while being stirred continuously, to evaporation at a temperature between 50° and 60° C. at a pressure between 2660 and 6650 Pas, until its saccharimetric degree stabilises between 70° and 80° Brix;
b) the syrup thus obtained is cooled at a temperature between 15° and 25° C. and mixed with 5 to 10 parts by weight, with respect to the weight of the lactulose contained in the syrup, of ore pulp obtained from the processing cycle;
c) the suspension thus obtained is kept stirring at 10° C., for a time between 150 and 400 hours, until complete crystallisation of the lactulose;
d) the crystallised lactulose is separated from the mother liquors by centrifugation or filtration, washed with cold water and dried at a temperature between 30° and 60° C., with a pressure of 6650-13300 Pas until a crystalline lactulose is obtained with a water content of less than 0.5%.

Part of the ore pulp is used to trigger the crystallisation of the next load of commercial syrup of lactulose.

The crystalline lactulose is separated at the end of the process by centrifugation or filtration with a yield of 40-50%, with respect to the lactulose contained in the commercial syrup, and a purity higher than 98.5%.

Commercial syrups generally contain from 50 to 70% lactulose, preferably 55-62%.

The crystalliser is seeded with 5-10% ore pulp, the equivalent of 2-4% lactulose (expressed as anhydrous lactulose) referred to the lactulose contained in the commercial syrup.

The main advantages with respect to the Applicant's previous patents EP 318.630 and EP 622.374, which are the closest prior art, may be summed up as follows:
possibility of using any commercial syrup of lactulose as the starting product;
possibility of working in a continuous cycle, using the lactulose crystallisation suspension as a triggering agent, without having to prepare and add to syrup crystalline lactulose trihydrate prepared separately This implies a considerable simplification of the industrial process;
very high purity of the crystalline lactulose with yields notably higher when using the same starting commercial syrup.

We shall now give an illustrative example of an industrial embodiment of the new process according to the invention, though it is clear that the operative procedures may vary considerably, depending on the lactulose syrup used as the starting raw material.

EXAMPLE

A) Preparation of the First Triggering Ore Pulp for Starting Up the System

To prepare this first suspension purified water and dry lactulose crystal are used, in a proportion of 28-32% water and 68-72% crystalline lactulose. 1300 kg of water are loaded, heated to a temperature of 37±2° C. and, while stirring, crystalline lactulose is added, with purity 99.3% in a quantity of 3.025 kg.

This is brought to a temperature of 40-45° C. and the agitator is kept running until the crystalline lactulose has completely dissolved.

4,325 kg of solution are obtained at a concentration of 71.2° Brix. Purified water is added while stirring, until a concentration of 70.0° Brix is reached for a lactulose content of 67.9% and a total ore pulp weight of 4.400 kg.

The temperature of the solution has been lowered to 10° C. and kept at this level, still stirring.

The lactulose begins to crystallise and, as it falls, the degrees Brix of, the mother liquors decrease. After 8 days the degrees Brix of the mother liquors are 56.2° Brix and the ore pulp may be used to seed the crystallisers containing concentrated syrup of lactulose.

3,500 kg of ore pulp are obtained at 71.1% lactulose.

B) Crystallisation of the Lactulose 14.536 kg of an aqueous syrup of lactulose at 50% p/p were used, that is containing 7,287 kg of lactulose.

The syrup was first of all concentrated by evaporating 2,946 kg of water, at a syrup temperature of 60° C.

In about 12 hours 11,590 kg of a concentrated solution were obtained, presenting a value of 76° Brix and containing 62.8% lactulose, equal to 7,279 kg of lactulose.

At this point the temperature of the concentrated syrup is lowered to 21±1° C. and crystallisation is triggered by adding ore pulp of lactulose, prepared as described above.

To do this, still stirring, 430 kg of ore pulp at 71.1% lactulose are added, equal to 306 kg of lactulose.

In this way 12,020 kg of total suspension are obtained, with a lactulose concentration of 63.1% p/p and a Brix value of 75.5°.

It is further cooled from 21° to 8° C. causing the growth and separation of the lactulose crystals and the consequent lowering of the degrees Brix of the mother liquors.

The crystallised lactulose suspension is ready for centrifugation when the concentration of the mother liquors falls within the limits of the specification with values of degrees Brix between 64.0 and 69.0 while the temperature is maintained between 9° and 15° C.

In the specific case, when the refraction index of the mother liquors indicated a concentration of 67.5° Brix, the suspension was centrifuged, separating the crystallised lactulose from the mother liquors and leaving 430 kg of ore pulp in the crystalliser as a triggering agent for the next crystallisation.

A) In the Specific Case, the Crystallised Lactulose was Separated by Centrifugation.

11,590 kg of product from phase (B) were centrifuged and 3,873 kg of humid lactulose were obtained.

The centrifuged product was analysed after the 1$^{st}$ and after the 14$^{th}$ centrifugation. The product composition found is shown in the following table where
LTL=lactulose, LTS=lactose, GLT=galactose,
TGT=tagatose, EPL=epilactose, FRT=fructose
KF=residual humidity, N.D.=not determinable.

a) Drying

The centrifuged product is dried at a temperature ≤60° C. and drying continues until a humidity percentage ≤2% is reached. In the specific case drying took 7 hours. After this time the temperature was lowered gradually and the finished product was unloaded.

3,181 kg of crystalline lactulose were obtained with 99.8% purity, equal to a yield of 43.8% on 7,268 kg of lactulose present in the starting commercial syrup. This yield is highly significant with respect to the yields that can be obtained with the patents EP 318.630 and EP 622.374 with which a maximum yield of 28% is achieved.

The invention claimed:

1. A process for continuous preparation of anhydrous crystalline lactulose from an aqueous syrup containing it, which has been concentrated to a saccharimetric degree of from 70° to 80° Brix, comprising mixing a mother liquor left following separation of lactulose crystals from a previous, lactulose crystallisation phase, said mother liquor having a saccharimetric index of from 64.0° to 69.0° Brix, with said aqueous syrup to trigger crystallisation of lactulose without the addition of any crystalline triggering agents from outside said process, and separating said anhydrous crystalline lactulose in high yield and highly purified form therefrom.

2. Process according to claim 1, wherein the aqueous syrup contains up to 10-30% of carbohydrates other than lactulose.

3. The process according to claim 1, comprising adding said mother liquor to said syrup in an amount ranging from 5%-10% by weight of the lactulose present in said syrup.

4. The process of claim 1, comprising adding said mother liquor in an amount ranging from 5%-10 and containing 2%-3% p/p of lactulose relative to lactulose present in said syrup.

5. The process of claim 1, further comprising stirring said aqueous syrup at 15-25° C. while adding said mother liquor.

6. The process of claim 1, further comprising cooling said aqueous syrup following triggering of crystallisation to a temperature of from 8° C. to 15° C., and maintaining said aqueous syrup at said temperature for from about 150 to about 400 hours.

7. The process of claim 1, further comprising stopping crystallisation when the saccharimetric index of said mother liquor reaches a degree from 64.0° to 69.0° Brix.

8. The process of claim 7, comprising stopping crystallisation when the saccharimetric index of said mother liquor is about 67.5° Brix.

9. The process of claim 6, comprising maintaining said aqueous syrup at a temperature of about 10° C.

10. The process of claim 1, further comprising separating said crystallized lactulose via centrifugation.

11. The process of claim 10, wherein said crystallized lactulose has a residual humidity of 10-15%.

| Processing | N.analysis | LTL % | LTS % | GLT % | TGT % | EPL % | FRT % | KF |
|---|---|---|---|---|---|---|---|---|
| 029/07-01 | 2379/01 | 99.3 | N.D. | N.D. | N.D. | N.D. | N.D. | 15.1 |
| 029/07-14 | 2428/07 | 99.8 | N.D. | N.D. | N.D. | N.D. | N.D. | 14.7 |

12. The process of claim 11, further comprising drying said crystallized lactulose at a temperature less than 60° C. for a time sufficient to reach residual humidity of less than 2%.

* * * * *